US007560689B2

(12) United States Patent
Ban et al.

(10) Patent No.: US 7,560,689 B2
(45) Date of Patent: Jul. 14, 2009

(54) HIGH-SENSITIVITY MASS SPECTROMETER AND METHOD

(75) Inventors: Kazuhiro Ban, Tokyo (JP); Hiroyuki Hashimoto, Yokohama (JP); Manabu Komatsu, Kawasaki (JP); Norihiko Utsunomiya, Tokyo (JP); Yohei Murayama, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 260 days.

(21) Appl. No.: 11/682,500

(22) Filed: Mar. 6, 2007

(65) Prior Publication Data

US 2008/0073509 A1 Mar. 27, 2008

(30) Foreign Application Priority Data

Mar. 10, 2006 (JP) ............................ 2006-066026

(51) Int. Cl.
*B01D 59/44* (2006.01)
*H01J 49/00* (2006.01)
*H01J 49/40* (2006.01)
*G01N 31/00* (2006.01)
*G01N 33/00* (2006.01)
*G01N 23/00* (2006.01)
*G21K 7/00* (2006.01)

(52) U.S. Cl. ...................... 250/288; 250/287; 250/281; 250/282; 250/289; 250/304; 250/309

(58) Field of Classification Search ................. 250/287, 250/288, 281, 282, 289, 304, 309; D24/216
See application file for complete search history.

(56) References Cited

U.S. PATENT DOCUMENTS 5,808,300 A * 9/1998 Caprioli ...................... 250/288
6,756,586 B2 * 6/2004 Caprioli ...................... 250/281
7,078,687 B2 7/2006 Uenishi et al. .............. 250/306
7,439,497 B2 * 10/2008 Dantus et al. ............... 250/288
2004/0026630 A1 * 2/2004 Mohun et al. ............ 250/458.1
2004/0251412 A1 * 12/2004 Tappel ........................ 250/304
2007/0105087 A1 * 5/2007 Ban et al. ...................... 435/4

FOREIGN PATENT DOCUMENTS

JP 2004-219261 8/2004
WO WO 2005/003715 A2 6/2001

OTHER PUBLICATIONS

Schwartz et al. ("Direct tissue analysis using MALDI MS: practical aspects of sample preparation" Journal of Mass Spec. 2003; 38; 699-70).*

Brandt et al. ("A simple, chisel-assisted mechanical microdissection system for harvesting homogenous plant tissue suitable for the analysis of nucleic acids and proteins" Plant Molecular Bio. Reporter, 21: 417-4.*

Analytical Chemistry, vol. 74, No. 19, "Organic Secondary Ion Mass Spectrometry: Sensitivity Enhancement By Gold Deposition", Oct. 2002, pp. 4955-4968.

* cited by examiner

*Primary Examiner*—Jack I Berman
*Assistant Examiner*—Brooke Purinton
(74) *Attorney, Agent, or Firm*—Fitzpatrick, Cella, Harper & Scinto

(57) ABSTRACT

A sample is sliced obliquely with a blade provided with a metal thin film on the surface, and the slice of the sample adhering to the blade surface is subjected to mass spectrometry. As a result, the section of the sliced sample can be analyzed immediately by mass spectrometry with high sensitivity.

10 Claims, 13 Drawing Sheets

ON Si WAFER

ON GOLD SUBSTRATE

FIG. 3
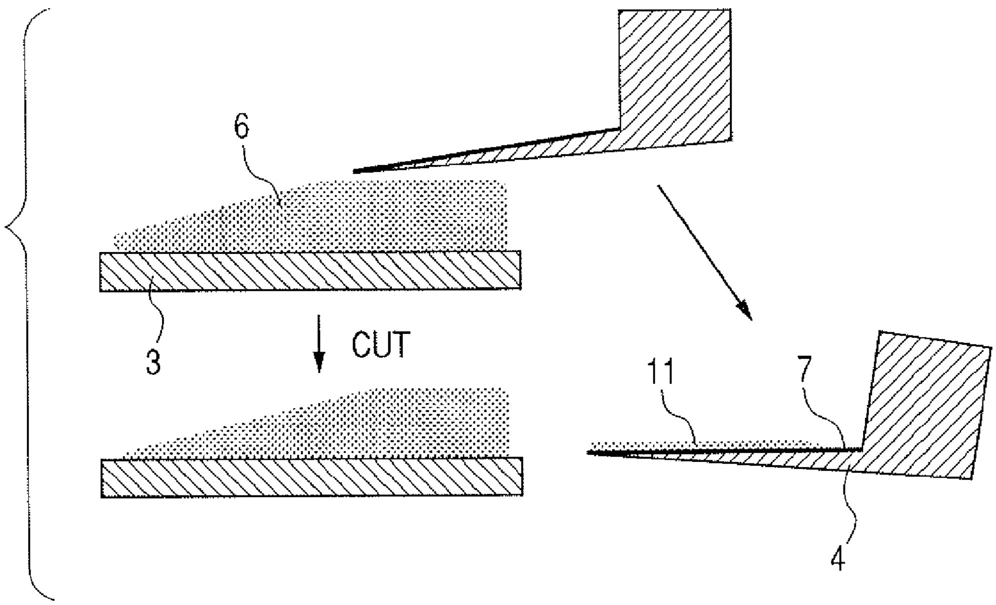
FIG. 4A
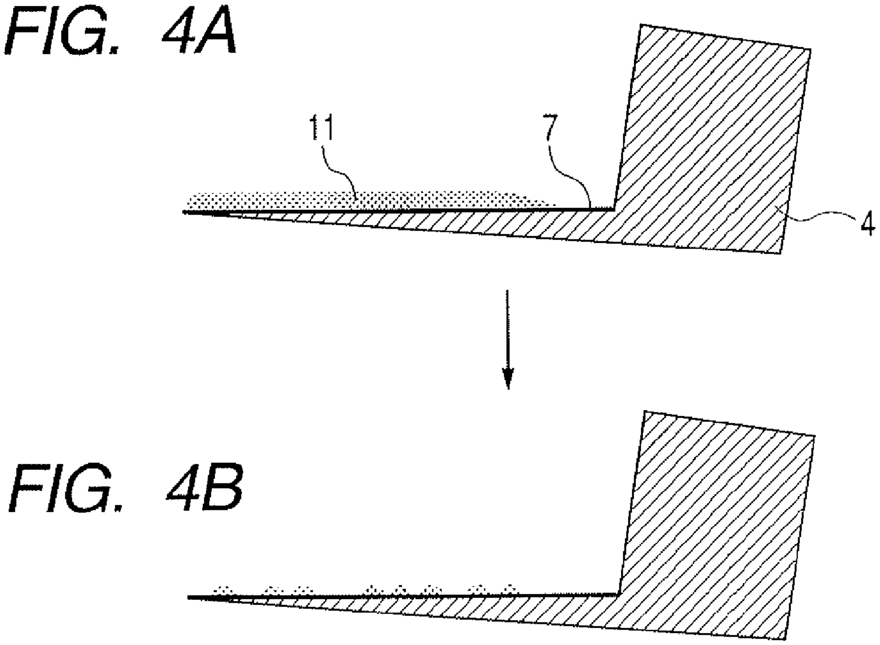
FIG. 4B $PO_3$ IMAGE

POLYPEPTIDE IMAGE $PO_3$ IMAGE

POLYPEPTIDE IMAGE $PO_3$ IMAGE

POLYPEPTIDE IMAGE

PO3 IMAGE

POLYPEPTIDE IMAGE

HIGH-SENSITIVITY MASS SPECTROMETER AND METHOD

BACKGROUND OF THE INVENTION

1. Field of the Invention

The present invention relates to an apparatus and a method wherein a sample is cut with a blade having a metal thin film on the surface at least in part, and the slice of the sample adhering to the blade surface is subjected to mass spectrometry.

2. Description of the Related Art

The importance of analysis of proteins as gene products existing in vivo is rapidly coming to the fore with progress in genome analysis in recent years. Particularly, the importance of protein analysis in tissue slices is pointed out. For example, many attempts have been made to elucidate proteins associated with recurrence or metastasis from cancer tissue slices. Protein analysis approaches with biological samples are generally performed according to the following procedures:

(1) extraction of proteins from biological tissues or cells;
(2) separation of the proteins from the extracts (solutions);
(3) analysis of the separated proteins or (poly)peptides as degradation products thereof; and
(4) identification of the obtained analysis result.

While a variety of protein analysis methods are known, time-of-flight mass spectrometry has received attention as a method capable of accurately analyzing trace amounts of samples. The pamphlet of International Publication of WO2005/003715 discusses an information acquisition method and apparatus based on TOF-SIMS (time-of-flight secondary ion mass spectrometry), which are directed to visualizing the two-dimensional distribution of proteins in biological tissue slices. In this analysis method, a substance for promoting ionization and/or a digestive enzyme are directly added to biological tissue slices, and information about a protein type (including information about peptides resulting from partial hydrolysis by the digestive enzyme) is visualized by TOF-SIMS with the positional information thereof being held. Thus, this analysis method is not intended to immediately analyze the section of the cut biological tissue.

Japanese Patent Application Laid-Open No. 2004-219261 (corresponding to U.S. Patent Application Publication No. US-2004-0232330) discusses an approach, which involves analyzing, by mass spectrometry, a section of a multilayered thin film cut obliquely with a microtome and consequently analyzing the thin film with a high spatial resolution. On the other hand, Analytical Chemistry, 74 (2002), 4955-4968, "Organic secondary ion mass spectrometry: sensitivity enhancement by gold deposition" discusses a technique for improving the ionization efficiency of TOF-SIMS by gold deposition. A gold substrate is also known to produce ion sensitizing effect, even in the presence of a sample thereon, if the sample is thin to such an extent that the influence of an ion beam reaches the substrate.

Thus, if a slice of a sample cut with a microtome or SAICAS (surface and interfacial cutting analysis system) is transferred onto a metal substrate and subjected to mass spectrometry, molecules existing in the slice of the sample are efficiently ionized by the ion sensitizing effect. Therefore, improvement in sensitivity can be expected. However, the slice of the sample is not easy to transfer onto the substrate with good positional accuracy.

As discussed in Japanese Patent Application Laid-Open No. 2004-219261, the cut surface of a sample on a substrate is easily analyzed. However, the acquisition of ion sensitizing effect requires depositing a metal onto the section of the sample on the substrate after sample cutting. As a result, the metal is deposited even onto a portion in no need of deposition in the sample unless the portion is masked. One run of mass spectrometry on the sample surface on the substrate results in the degradation and volatilization of tissue degradation products within the sample due to high energy irradiation. Thus, the sample analyzed once on the substrate has morphological changes in both the surface and interior thereof caused by metal deposition and analysis. Such a sample had the problem of not serving as a proper analyte for obtaining additional information on the interior thereof.

SUMMARY OF THE INVENTION

An object of the present invention is to provide a mass spectrometer and a mass spectrometry method capable of performing high-sensitivity time-of-flight mass spectrometry and imaging of the analysis result while holding the positional accuracy of a slice of a sample existing on a blade after sample cutting with the blade.

To solve the problems, the present invention provides an apparatus and an approach capable of immediately analyzing the cut section of a sample by mass spectrometry with high sensitivity.

Specifically, the present invention provides a mass spectrometer including: a slice preparing section for preparing a slice of a sample for analysis; and a mass spectrometry section for performing time-of-flight mass spectrometry on the slice of the sample prepared in the slice preparing section, wherein the slice preparing section includes: a sample holding mechanism for holding a sample; a blade having a metal thin film on the surface at least in part; and a blade position control mechanism for controlling the position of the blade and thereby performing both sample cutting and mounting of the slice of the sample obtained by cutting onto the blade surface, and wherein the mass spectrometry section includes: a blade holding mechanism for holding the blade; and a beam irradiation mechanism for irradiating the blade surface having the slice of the sample mounted thereon with one of pulse laser and pulse ion beams.

The present invention also provides a mass spectrometry method for performing time-of-flight mass spectrometry including irradiating a slice of a sample with one of pulse laser and pulse ion beams and thereby ionizing a molecule within the slice of the sample, wherein a sample is cut with a blade having a metal thin film on the surface at least in part, and the slice of the sample adhering to the blade surface is irradiated with one of pulse laser and pulse ion beams.

Further features of the present invention will become apparent from the following description of exemplary embodiments with reference to the attached drawings.

BRIEF DESCRIPTION OF THE DRAWINGS

FIG. 1A illustrates the result on a Si wafer, and FIG. 1B illustrates the result on a gold substrate.

FIG. 2A illustrates a step of cutting a sample, and FIG. 2B illustrates a step of irradiating the slice of the sample with an ion beam.

FIG. 3 is a schematic view illustrating one example of a manner to obliquely cut a biological tissue with a blade.

FIGS. 4A and 4B are respectively a schematic view illustrating one example of a biological tissue slice. FIG. 4A illustrates its state during freezing and immediately after cutting, and FIG. 4B illustrates its state at room temperature and after water evaporation.

FIG. 5A illustrates a $PO_3$ image, and FIG. 5B illustrates a polypeptide-specific image.

FIG. 6A illustrates a $PO_3$ image, and FIG. 6B illustrates a polypeptide-specific image.

FIG. 7A illustrates a step of cutting a biological tissue with a blade A, FIG. 7B illustrates a step of subjecting the slice of the biological tissue cut with the blade A to mass spectrometry while further cutting the biological tissue with a blade B, and FIG. 7C illustrates a step of subjecting the slice of the biological tissue cut with the blade B to mass spectrometry.

FIG. 8A illustrates cutting with the blade A, and FIG. 8B illustrates cutting with the blade B.

FIG. 9A illustrates its state during freezing and immediately after cutting, and FIG. 9B illustrates its state at room temperature and after water evaporation.

FIG. 10A illustrates a $PO_3$ image, and FIG. 10B illustrates a polypeptide-specific image.

FIG. 11A illustrates its state during freezing and immediately after cutting, and FIG. 11B illustrates its state at room temperature and after water evaporation.

FIG. 12A illustrates a $PO_3$ image, and FIG. 12B illustrates a polypeptide-specific image.

FIG. 14A illustrates a step of cutting a sample, FIG. 14B illustrates a step of supplying an enzyme solution onto a slice of the sample, and FIG. 14C illustrates a step of irradiating the slice of the sample with an ion beam.

DESCRIPTION OF THE EMBODIMENTS (Construction of Apparatus)

Figure 13:
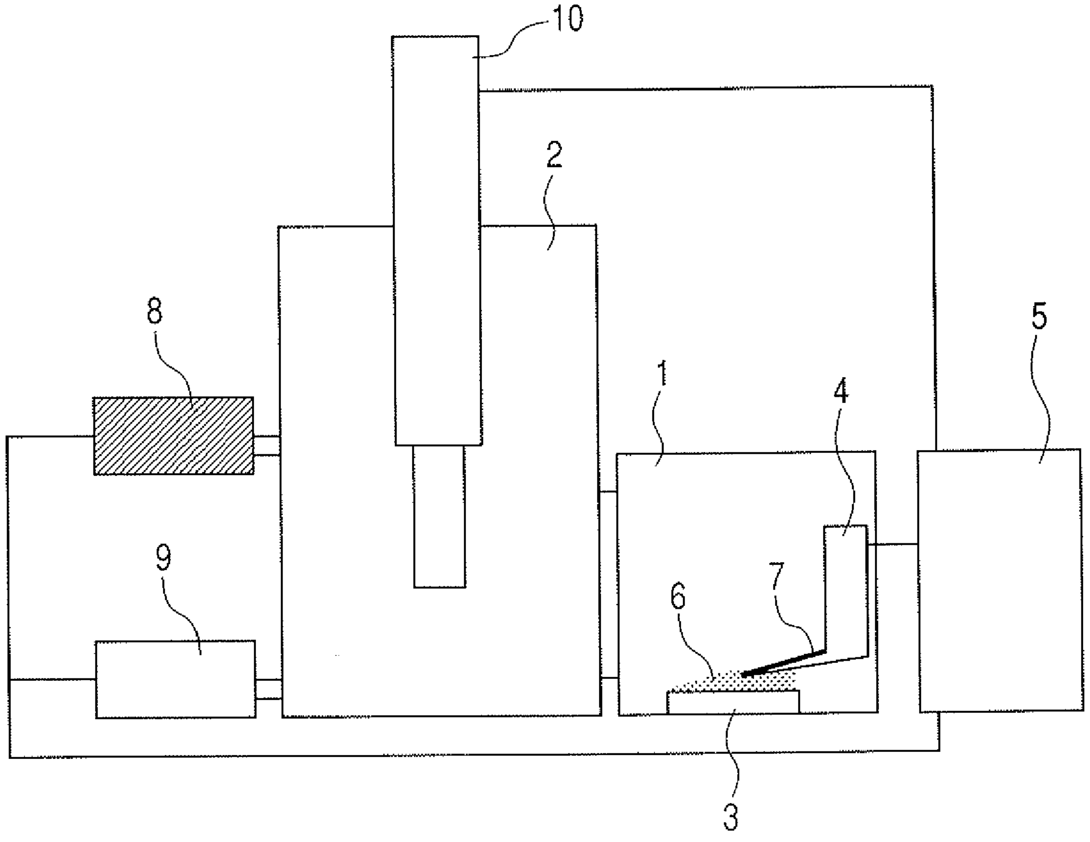
FIG. 13 is a schematic view illustrating one example of a mass spectrometer related to the present invention.

A mass spectrometer of the present invention includes at least: a slice preparing section 1 for preparing a slice of a sample; and a mass spectrometry section 2 for performing time-of-flight mass spectrometry on the slice of the sample prepared in the slice preparing section, as shown in FIG. 13. Hereinafter, each component of the apparatus will be described.

(Slice Preparing Section)

The slice preparing section is provided with at least a sample holding mechanism 3, a blade 4 and a blade position control mechanism 5.

(Sample Holding Mechanism)

The sample holding mechanism 3 has a mechanism for securely holding a sample 6 during sample cutting with the blade and can be constructed by utilizing a sample holding mechanism used in slice preparation. For example, a sample holder used in a microtome or SAICAS can be utilized as the sample holding mechanism.

(Blade and Blade Position Control Mechanism)

The blade 4 to be used has a structure in which a slice of a sample obtained by cutting the sample held in the sample holding mechanism can be mounted on a predetermined surface of the blade. In the present invention, the slice of the sample mounted on the blade surface is irradiated with a beam for mass spectrometry. Therefore, the blade is selected from those adapted to the beam irradiation treatment. Any blade suitable to this purpose and usage may be employed. A commercially available microtome or SAICAS blade is preferably used. The microtome refers to a pretreatment apparatus for slicing samples for microscopic observation and includes sliding and rotary microtomes. The microtome is mainly used in pathology examination, wherein cells are generally cut with the microtome into a thickness of 2 or 3 microns and used in microscopic observation after staining with a reagent. Recently, the microtome is also frequently used in, for example, research on various materials. The cut surface of an object is flat with precision not larger than 1 micron and therefore, is also observed for research purposes. For example, the microtome is employed for observing the sections of photosensitive photographic films or observing the densities of rubber materials. SAICAS refers to a system for cutting a material from the surface to the interior with a sharp blade and detecting a resistance arising in the blade. A commercially available SAICAS apparatus can measure a film thickness of 0.1 to 1000 μm. In principle, the SAICAS apparatus can cut a sample of at least 1 Å. In this context, the spatial resolution of the sample cutting is determined by blade position control ability. A proper film thickness is described later.

In the present invention, a metal thin film 7 is formed on the blade surface at least in part. The slice of the sample adhering to the thin film is irradiated with one of pulse laser and pulse ion beams to thereby efficiently ionize a molecule within the slice.

The metal thin film is provided on at least a region of the blade surface on which the slice of the sample is mounted. When the upper end of the sample is cut in a horizontal direction with the blade, the metal thin film can be provided on the upper surface of the blade and preferably, can be provided on the whole upper surface. This construction simplifies the construction of the apparatus.

Figure 1A:
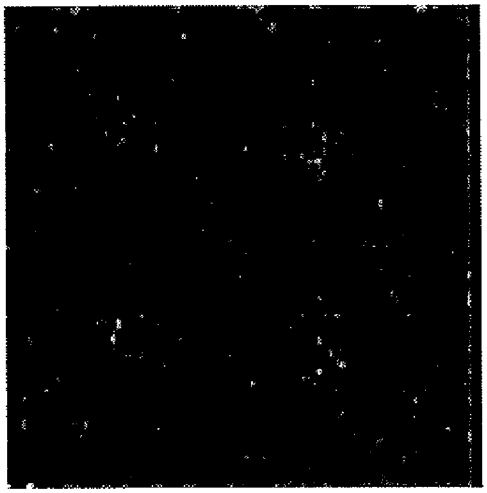
FIGS. 1A and 1B respectively illustrate a TOF-SIMS imaging result.
Figure 1B:

Diamond is generally used as a material for a blade in a microtome. In the present invention, metals such as stainless steels and titanium and porcelains such as glass and ceramics may be used as materials for the blade. Plastics may also be used for very soft samples. Those metals include, but not limited to, gold, silver, copper, platinum, or the like, as long as the effect described above is obtained. More specifically, a gold or silver thin film is used, and still more preferably, a gold thin film is used. It has come to our attention that when gold exists around a sample undergoing primary ion irradiation, it exerts excellent ion sensitizing effect in time-of-flight mass spectrometry. FIGS. 1A and 1B illustrate TOF-SIMS imaging profiles obtained by analyzing, under the same conditions, one and the same polypeptides spotted on a Si wafer and on a gold substrate, respectively.

Thus, a metal thin film including gold or the like is preferably provided on the upper surface of the blade, on which the slice of the sample is present. As a result, the secondary ionization of the sample is efficiently performed after primary ion beam irradiation. To form the thin film, the blade is placed in a chamber of an evaporation or sputtering apparatus with the upper surface thereof facing the target and is subjected to deposition or sputtering. The thickness of the thin film is preferably 1 nm or more. A film thickness less than 1 nm might be insufficient for efficiently ionizing a molecule within the slice. The under surface of the blade is preferably treated to prevent sample contents from adhering thereto during cutting. For example, the under surface is coated with skimmed milk, casein, serum albumin, phospholipids, polyethylene glycol and derivatives thereof to prevent unnecessary signals attributed to the adsorption of impurities by so-called nonspecific adsorption. Plural pieces of the blade described above can be prepared within the apparatus and position-controlled to thereby repeat sample cutting and mass spectrometry. This allows for the three-dimensional analysis of the sample.

The three-dimensional mass spectrometry method is not limited to the construction described above and may additionally use, for example, $C_{60}$ ions.

The blade can be used repetitively by providing a mechanism for exposing the metal thin film surface on the blade, such as a mechanism for washing the blade, within the apparatus.

Cutting operation for the sample with the blade is controlled by the blade position control mechanism. This blade position control mechanism can also be constructed by utilizing a blade position control mechanism used in a microtome or SAICAS.

A sample cutting space (region) and a pulse laser or pulse ion beam irradiation space (region) may be constructed integrally or separately within the apparatus. To perform these treatments in a single space (region), a slice preparing mechanism is provided in a beam irradiation space for mass spectrometry, that is, in an analysis chamber for performing mass spectrometry. This structure further allows the sample remaining after slice preparation to be taken out of the analysis chamber.

When these spaces are separately provided, the spaces can be controlled individually according to the purposes thereof. In this case, the slice preparing region provided with the sample holding mechanism and a region for conducting beam irradiation are provided so that these regions are each capable of independently being subjected to temperature- and humidity-control. For example, the analysis chamber for conducting beam irradiation needs to be kept in a high vacuum and requires a structure therefor. By contrast, the sample cutting space is prepared as a load lock chamber which is a space separate from the analysis chamber. For example, a substance in a liquid state at room temperature can be cut with the blade after freezing by controlling the temperature and humidity of this load lock chamber. The load lock chamber can be equipped with a refrigeration system, as in a commercially available freezing microtome, and thereby cooled. After vacuum control, the sample blade can be transferred to the analysis chamber and placed at the position of beam irradiation to thereby analyze the slice of the sample. To image an analysis result in agreement with the slice of the sample mounted on the blade surface, the blade surface is placed directly below a detector. The blade may be transferred automatically between chambers by utilizing a controller 5 as described in FIG. 13. In this case, conditions such as the degree of vacuum in each chamber may be adjusted appropriately in conjunction with the open/close operation of a gate between chambers. Moreover, cutting may be automated. This construction may further be provided with a mechanism for controlling cutting speed by voltage control while monitoring physical parameters such as resistance applied to the blade during cutting.

(Sample)

The sample of the present invention may be of any material and morphology and is preferably a biological tissue or cell.

The biological tissue or cell used as the sample may be treated with an enzyme. Trypsin is mainly used as the enzyme. In proper procedures, the biological tissue or cell, which is rich in moisture, is frozen and then cut. Therefore, most of the slice contents on the blade are water. Therefore, the thickness of the slice of the sample after water evaporation is much thinner than that in a frozen state during cutting.

In the present invention, a sample thickness from the surface after sample cutting is preferably 10 nm to 10000 nm, more preferably 10 nm to 1000 nm, from these viewpoints. The upper and lower limits of this region are set for the following two reasons:

(1) Reason for the lower limit set

Most proteins (less than 10 nm in size) in a saline are not cut in this range.

(2) Reason for the upper limit set

An ion beam easily reaches the surface of the metal thin film if organic samples having a thickness on the order of several tens of nm are used. As a result, the metal thin film exerts ion sensitizing effect described later.

When the sample morphology is a biological tissue or cell, water constitutes most of the contents thereof and evaporates during vacuum measurement. The upper limit of the range is set for the reason, in addition to the reason (2), that the slice in a vacuum after water evaporation has a thickness on the order of several % to 30% of that during freezing. Specifically, a sample thickness not more than 100 nm in cutting can be converted to a thickness not more than several tens of nm in ion beam irradiation. In the mass spectrometry of substances such as proteins adhering onto the blade by water evaporation, many molecules seem to be efficiently ionized by the ion sensitizing effect, and the mass spectrometry is successfully performed.

(Droplet Supplying Mechanism)

A droplet supplying mechanism 13 is provided in a mass spectrometer of the present invention in order to supply a solution to a sample slice having adhered to the blade surface in the sample cutting operation while keeping the positional precision.

The droplet supplying mechanism can be located in the same chamber as that of the slice preparing section or the mass spectrometry section, but preferably, it is located in a separate chamber so that it can be used under the conditions of ambient temperature and atmospheric pressure. More preferably, the chamber is capable of controlling the humidity. It is further preferable that the chamber is capable of being evacuated after the operation of treating a solution. The droplet supplying mechanism is preferably in the form of an ink jet apparatus, which may be of piezo type or of bubble jet type. While the solution containing a digestive enzyme is different from an ink in a strict sense, the term "ink jet" may simply be used below when the same apparatus or method as that for ink jet printing is used except for the solution to be supplied.

A solution containing an enzyme such as pepsin, trypsin, chymotrypsin, etc. can be used for decomposing proteins in a sample slice to carry out mass spectrometry in a high sensitivity region. Preferably, the amount and the distance when supplying a solution are controlled so that droplets of the supplied solution will not contact with each other.

(Time-of-Flight Mass Spectrometry Section)

A mass spectrometer used in the mass spectrometry section 2 for performing time-of-flight mass spectrometry may be constructed to enable mass spectrometry of the slice of the sample mounted on the blade surface. For example, the mass spectrometry section can be constructed by using at least the following components:

(1) an analysis chamber 2 having a holder for holding a slice of a sample;

(2) a beam irradiation unit 8 having a beam source for irradiating the slice of the sample with a beam and an optical system for irradiating a predetermined position with the beam;

(3) an atmosphere adjustment unit 9 for adjusting an atmosphere within the analysis chamber to a measurement condition (vacuum); and (4) a detector 10 for a secondary ion.

Alternatively, the slice preparing section and the analysis chamber may be the same space, as described above.

An ion generated from the beam irradiation of the slice of the sample on the blade surface is detected by MALDI-TOFMS (matrix assisted laser desorption/ionization time-of-flight mass spectrometer) or TOF-SIMS. As a result, the sample can be analyzed by mass spectrometry with the positional information thereof being held. This is performed by allowing the detector to suck, in a moment, the ion generated from beam irradiation, scanning the irradiation position and the detection position, and repeating irradiation and detection. The beam has preferably a pulse width of picosecond to nanosecond order. This can enhance a peak resolution in molecular weight detection.

One of pulse laser or pulse ion beams is used as the beam.

To perform mass spectrometry on a sample of a biological tissue or cell level in size, TOF-SIMS can be used. TOF-SIMS allows for mass spectrometry imaging with a spatial resolution of a submicron level. Therefore, a cell from which the detected ion is derived can be determined easily. If necessary, a substance for promoting ionization (sensitizing substance) disclosed by the present inventors in the pamphlet of International Publication of WO2005/003715 may be added thereto. General liquid metal ions such as $Ga^+$ as well as cluster ions such as $C_{60}$, $Au_3^+$ and $Bi_3^+$ can be used as primary ions.

EXAMPLES

Example 1

Figure 2A:
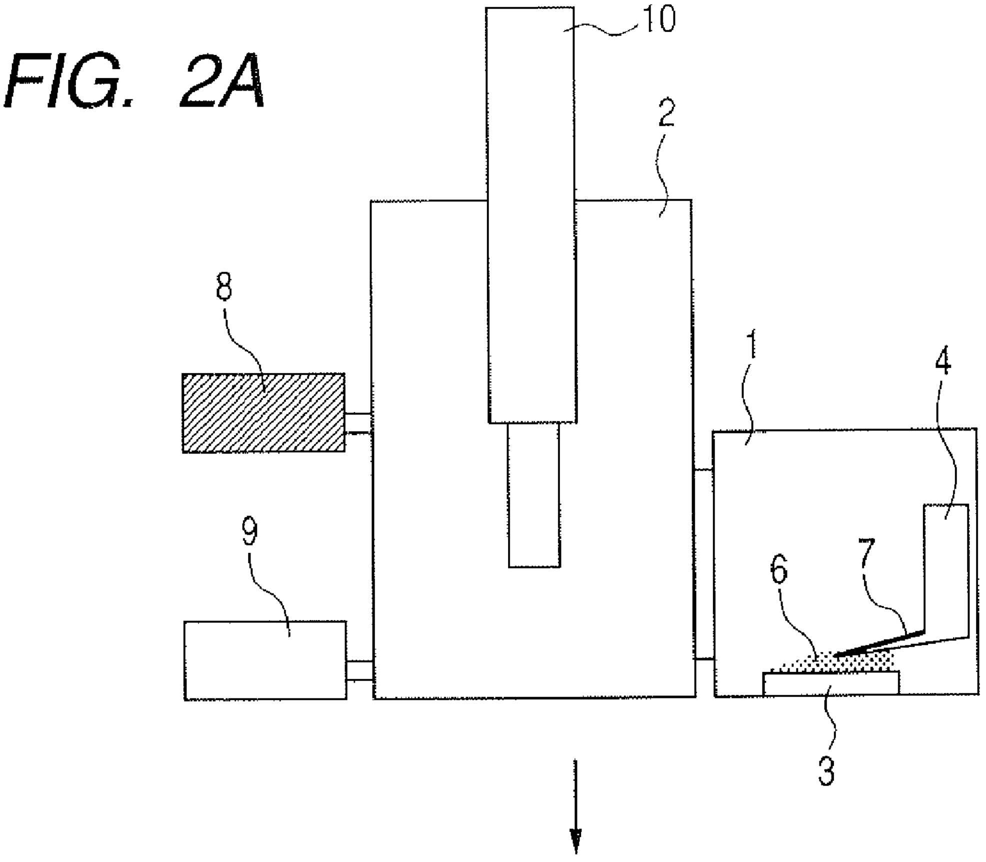
FIGS. 2A and 2B are respectively a schematic view illustrating one example of the operation of a mass spectrometer used in Example 1 of the present invention.
Figure 2B:
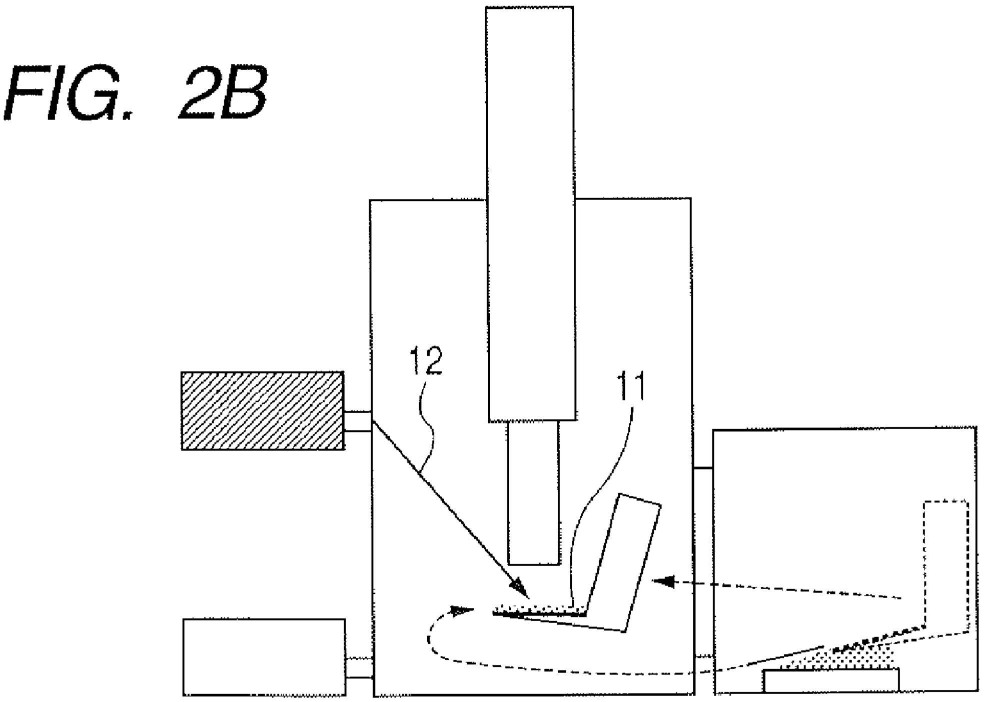

(TOF-SIMS analysis wherein a biological tissue is cut with a gold-deposited blade in a load lock chamber, and the blade having the biological tissue slice adhering thereon is transferred for the analysis to an analysis chamber, as shown in FIGS. 2A and 2B)

Figure 5A:
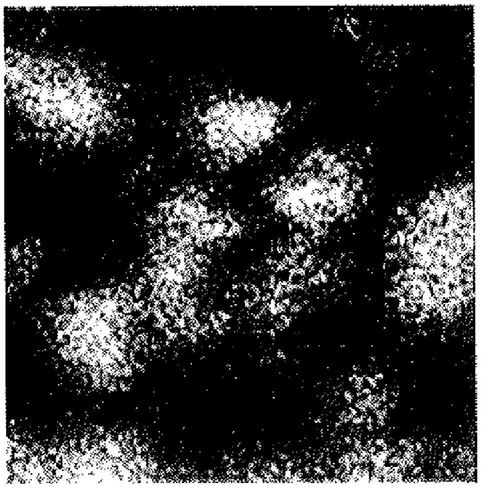
FIGS. 5A and 5B are respectively a diagram ideologically illustrating a possible TOF-SIMS imaging result in Example 1.
Figure 5B:
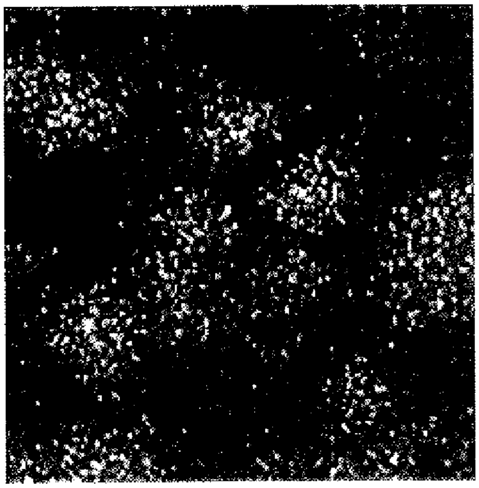

TOF-SIMS analysis is conducted on polypeptides of a slice of a biological tissue cut with a gold-deposited blade. A biological tissue 6 (human cancer tissue: Tissue Microarray Human Tumor Tissue (Lymphoma)) is allowed to adhere onto a Si substrate 3, which is held in a load lock chamber 1 (FIG. 2A). A temperature in the load lock chamber in which the substrate is held is set to −80° C. to freeze the biological tissue. The thickness of the sample here is approximately 100 nm. A blade 4 provided with a gold thin film 7 on the upper surface is operated to obliquely cut the biological tissue as shown in FIG. 3. A slice 11 of the biological tissue adhering to the upper surface of the blade by cutting (FIG. 4A) is transferred directly below a TOF-SIMS detector 10 and placed in a horizontal position (FIG. 2B). In the analysis chamber 2 kept at room temperature and in an ultrahigh vacuum, water evaporates from the biological tissue adhering to the upper surface of the blade while the contents thereof stay adhering to the upper surface of the blade (FIG. 4B). The thickness of the sample here is approximately 20 nm. The sample surface is irradiated with a pulse ion beam (primary ion beam) 12. The slice contents of FIG. 4B are analyzed and imaged by mass spectrometry using two-dimensional scanning for detecting the generated secondary ion. Imaging results of cell membrane-derived $PO_3$ (FIG. 5A) and polypeptide-specific (FIG. 5B) images obtained by the analysis show the presence of polypeptides within a particular cell in the biological tissue.

Reference Example 1

Gold Thin Film-Free Version of Example 1

TOF-SIMS analysis is conducted on polypeptides of a slice of a biological tissue cut with a SAICAS apparatus having a blade free from gold deposition.

Figure 6A:
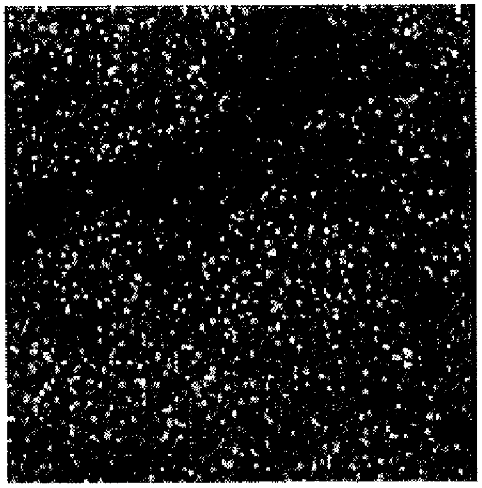
FIGS. 6A and 6B are respectively a diagram ideologically illustrating a possible TOF-SIMS imaging result in Reference Example 1.
Figure 6B:
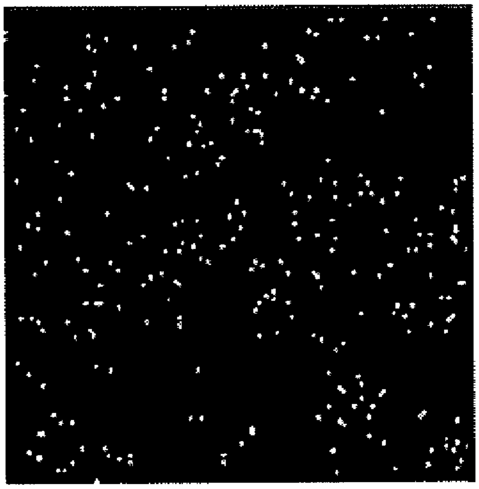

A biological tissue used is a human cancer tissue: Tissue Microarray Human Tumor Tissue (Lymphoma). This biological tissue is allowed to adhere onto a Si substrate and obliquely cut with a commercially available SAICAS apparatus at −80° C. The cut surface is transferred directly below a TOF-SIMS detector and placed in a horizontal position. The thickness of the sample here is approximately 100 nm. In the analysis chamber kept at room temperature and in an ultrahigh vacuum as in Example 1, water evaporates from the biological tissue adhering to the upper surface of the blade while the contents thereof stay adhering to the upper surface of the blade. The thickness of the sample here is approximately 20 nm. The sample surface is irradiated with a pulse ion beam. The slice contents of FIG. 4B are analyzed and imaged by mass spectrometry using two-dimensional scanning for detecting the generated secondary ion. A $PO_3$ image (FIG. 6A) obtained by the analysis is fewer than the $PO_3$ image of Example 1 (FIG. 5A), and a polypeptide-specific image (FIG. 6B) is hardly detected.

Example 2

Figure 7A:
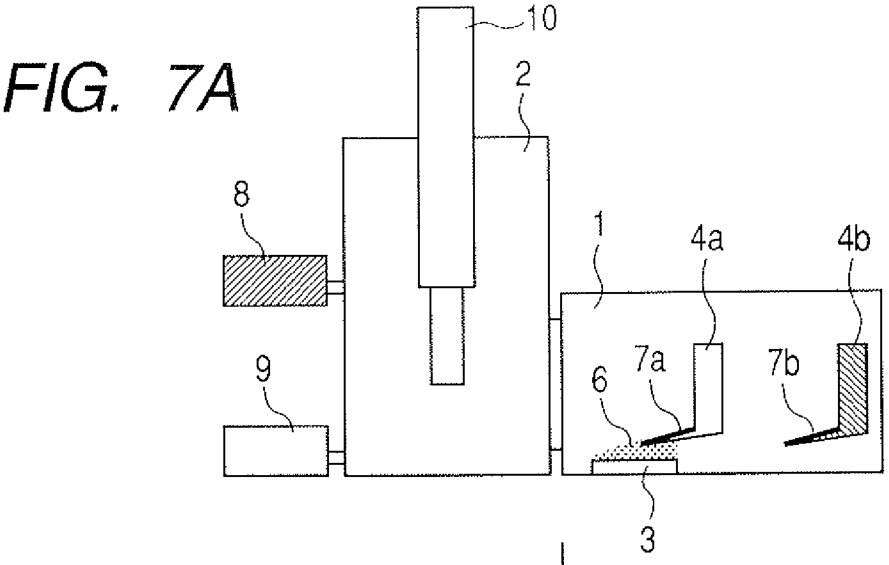
FIGS. 7A, 7B and 7C are respectively a schematic view illustrating one example of the operation of a mass spectrometer used in Example 2 of the present invention.
Figure 7B:
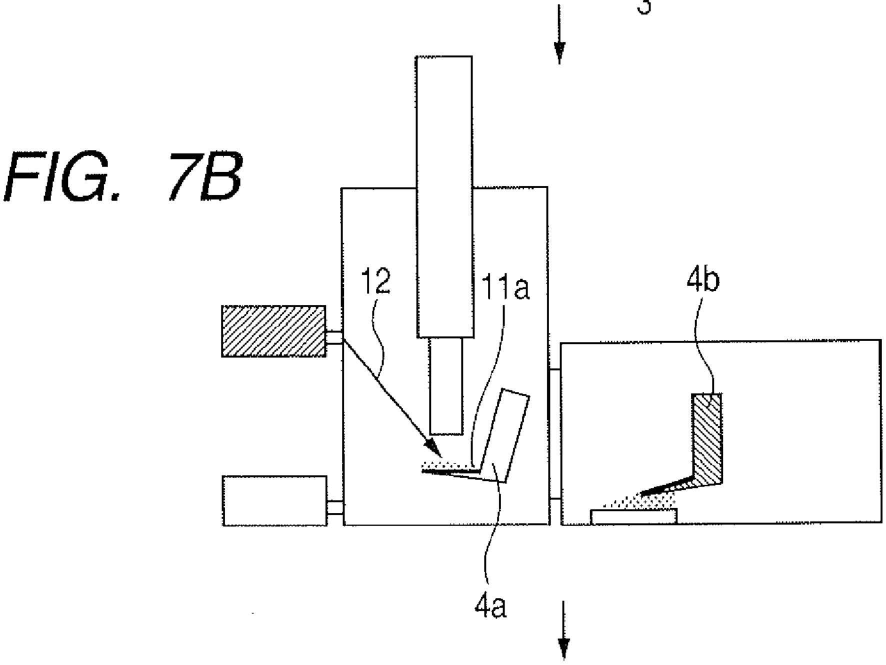
Figure 7C:
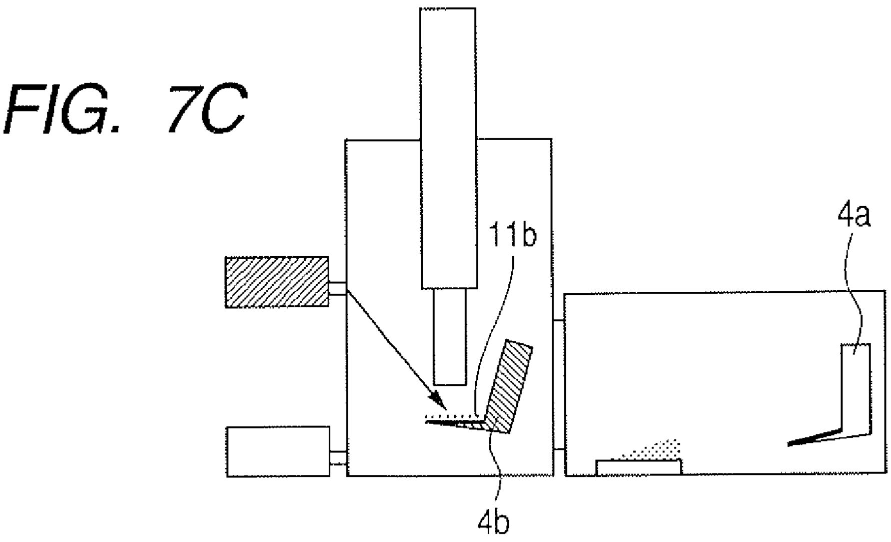

(Three-dimensional analysis of biological tissue by analysis of several slices obtained with several blades, as shown in FIGS. 7A to 7C)

Three-dimensional analysis is conducted on a biological tissue by subjecting, to TOF-SIMS analysis, polypeptides contained in several slices of the biological tissue cut several times with gold-deposited blades.

Figure 8A:
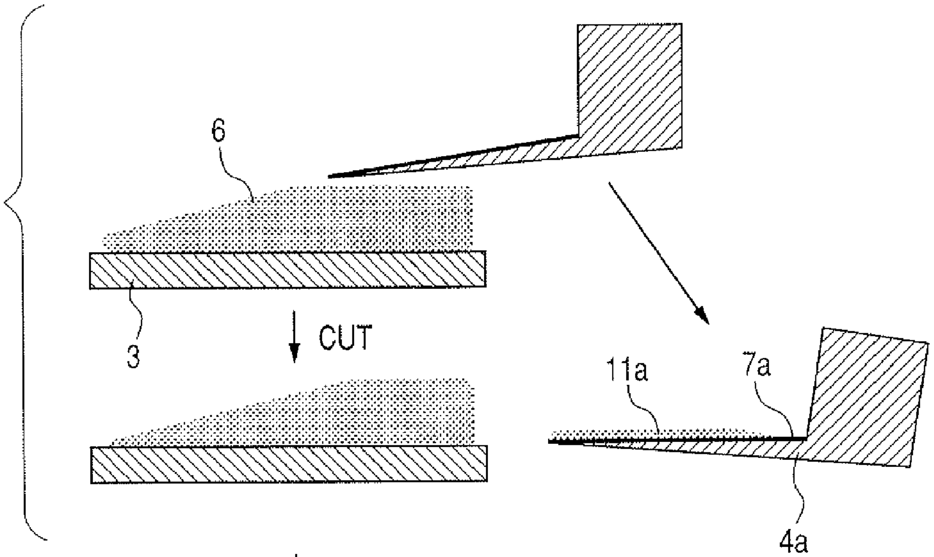
FIGS. 8A and 8B are respectively a schematic view illustrating one example of a manner to obliquely cut a biological tissue in Example 2.
Figure 9A:
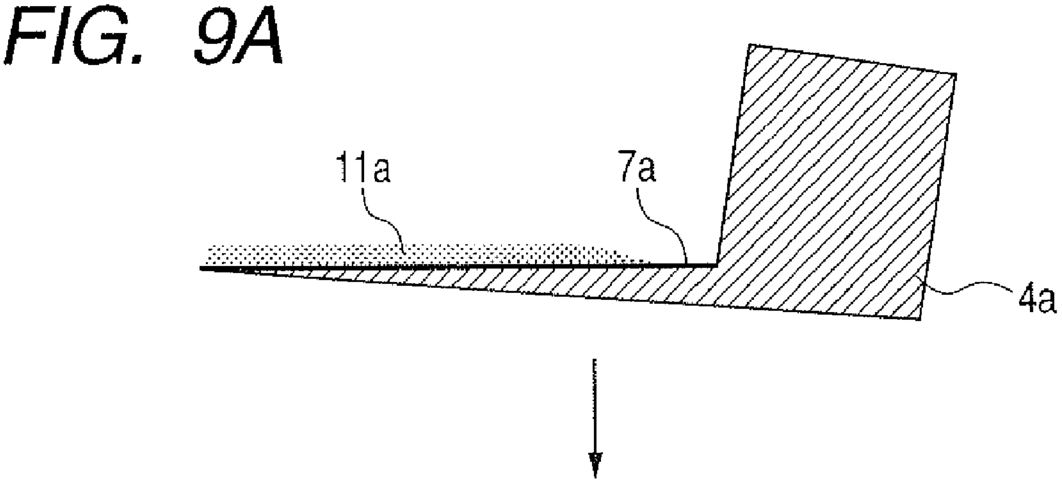
FIGS. 9A and 9B are respectively a schematic view illustrating one example of a biological tissue slice obtained with the blade A.
Figure 9B:
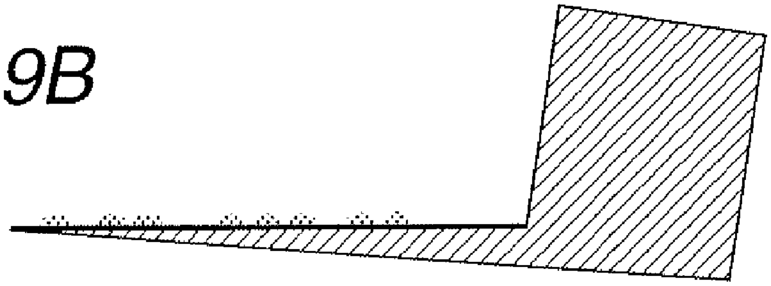
Figure 10A:
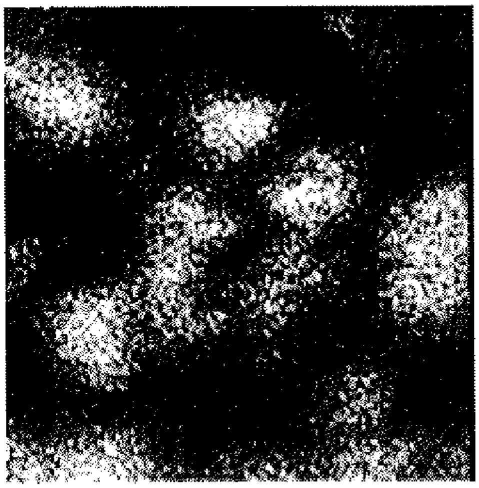
FIGS. 10A and 10B are respectively a diagram ideologically illustrating a possible TOF-SIMS imaging result of the blade A in Example 2.
Figure 10B:
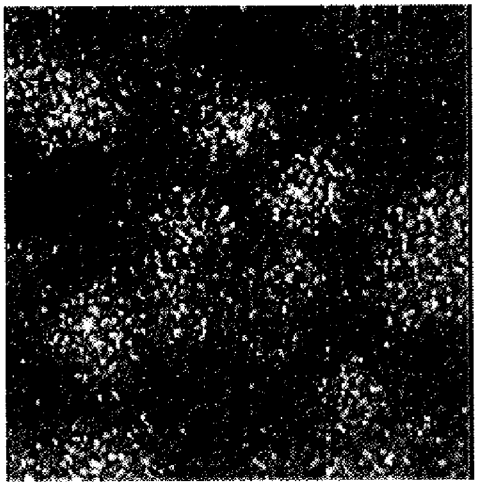

A biological tissue 6 (human cancer tissue: Tissue MicroArray Human Tumor Tissue (Colon Carcinoma)) is allowed to adhere onto a Si substrate 3, which is held in a load lock chamber 1 (FIG. 7A). A temperature in the load lock chamber in which the substrate is held is set to −80° C. to freeze the biological tissue. The thickness of the sample here is approximately 500 nm. A blade A (4*a*) provided with a gold thin film 7*a* on the upper surface is operated to obliquely cut the biological tissue as shown in FIG. 8A. A slice 11*a* of the biological tissue adhering to the upper surface of the blade by cutting (FIG. 9A) is transferred directly below a TOF-SIMS detector and placed in a horizontal position. In the analysis chamber kept at room temperature and in an ultrahigh vacuum, water evaporates from the biological tissue adhering to the upper surface of the blade while the contents thereof stay adhering to the upper surface of the blade (FIG. 9B). The thickness of the sample here is approximately 50 nm. The sample surface is irradiated with a pulse ion beam (primary ion beam) 12. The slice contents of FIG. 9B are analyzed and imaged by mass spectrometry using two-dimensional scanning for detecting the generated secondary ion (FIG. 7B). Imaging results of $PO_3$ (FIG. 10A) and polypeptide-specific images (FIG. 10B) obtained by the analysis show the presence of proteins within a particular cell in the slice of the biological tissue cut with the blade A.

Figure 8B:
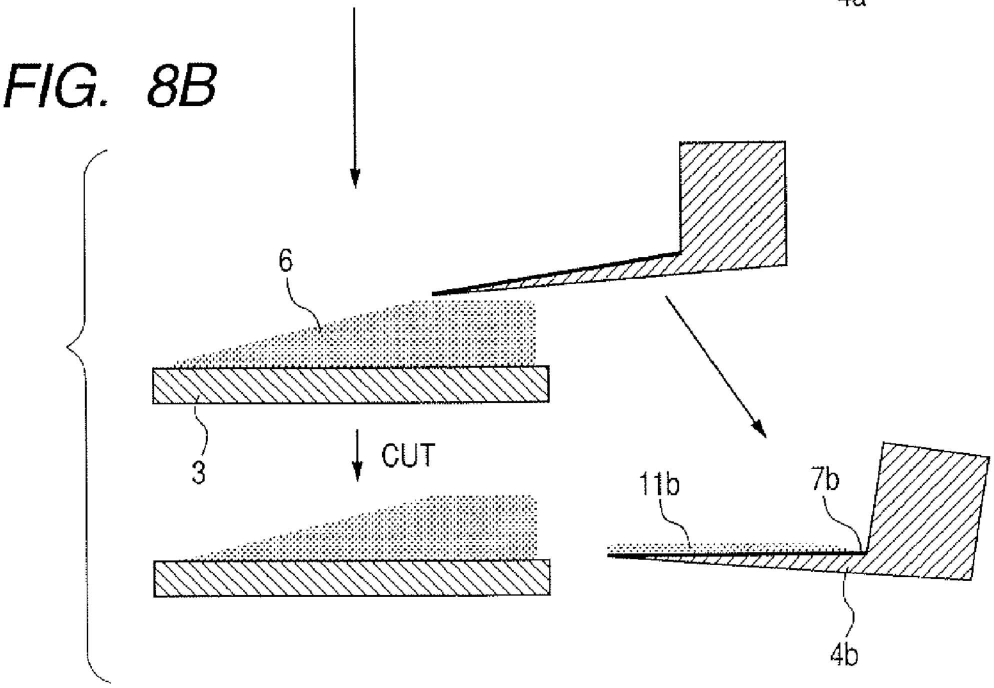
Figure 11A:
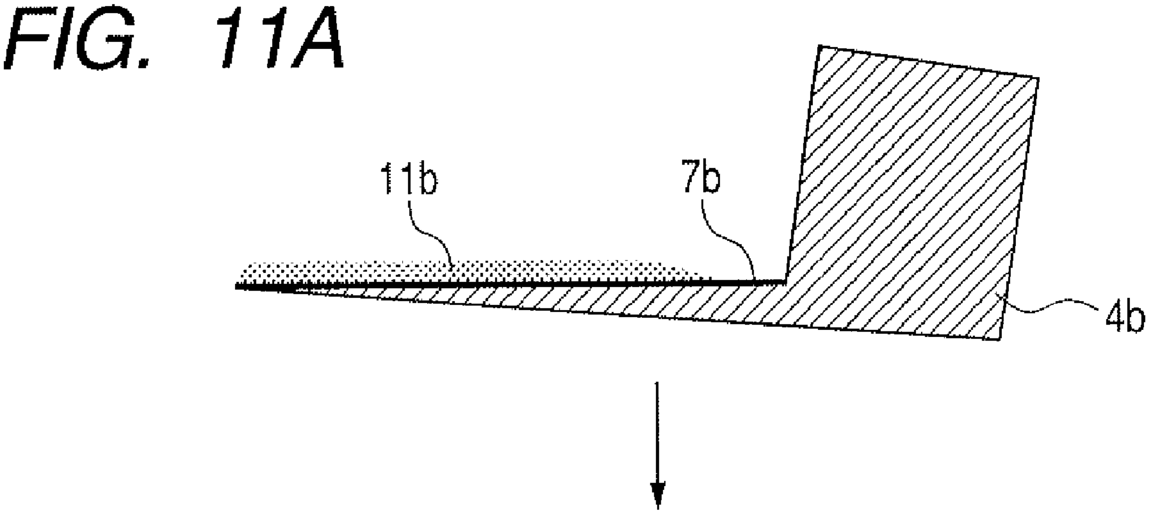
FIGS. 11A and 11B are respectively a schematic view illustrating one example of a biological tissue slice obtained with the blade B.
Figure 11B:
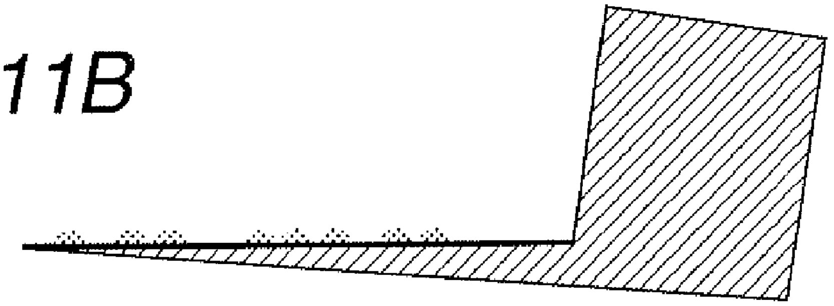
Figure 12A:
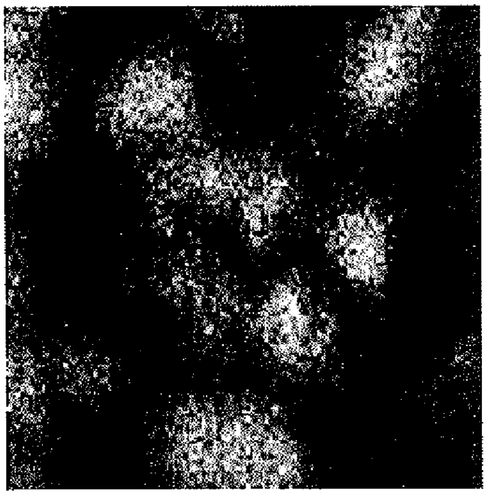
FIGS. 12A and 12B are respectively a diagram ideologically illustrating a possible TOF-SIMS imaging result of the blade B in Example 2.
Figure 12B:
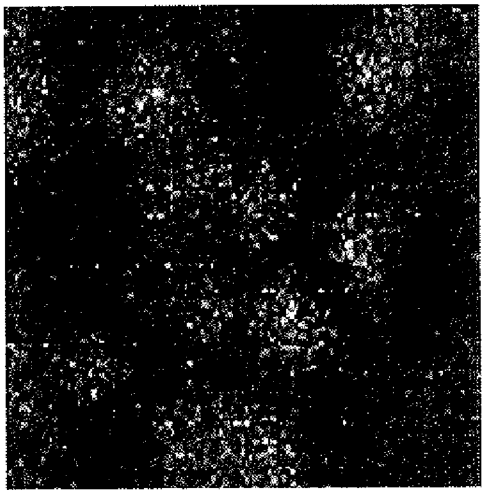

Subsequently, a blade B (4*b*) provided with a gold thin film 7*b* on the upper surface is operated to obliquely cut the biological tissue as shown in FIG. 8B (FIG. 7B). A slice 11*b* of the biological tissue adhering to the upper surface of the blade by cutting (FIG. 11A) is transferred directly below the TOF-SIMS detector and placed in a horizontal position. In the analysis chamber kept at room temperature and in an ultra-high vacuum, water evaporates from the biological tissue adhering to the upper surface of the blade while the contents thereof stay adhering to the upper surface of the blade (FIG. 11B). The sample surface is irradiated with the pulse ion beam (primary ion beam) 12. The slice contents of FIG. 11B are analyzed and imaged by mass spectrometry using two-dimensional scanning for detecting the generated secondary ion (FIG. 7C). Imaging results of $PO_3$ (FIG. 12A) and polypeptide-specific images (FIG. 12B) obtained by the analysis show the presence of polypeptides within a particular cell in the slice of the biological tissue cut with the blade B.

As described above, a biological tissue can be analyzed three-dimensionally by cutting the biological tissue several times with blades and subjecting several slices to TOF-SIMS analysis.

Example 3

Figure 14A:
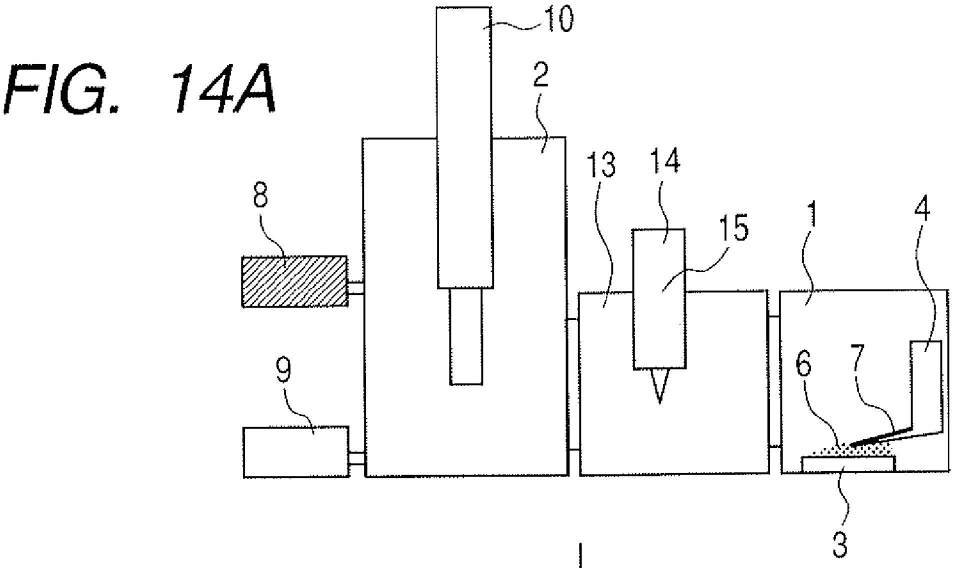
FIGS. 14A, 14B and 14C are respectively a schematic view illustrating one example of the operation of a mass spectrometer used in Example 3 of the present invention.
Figure 14B:
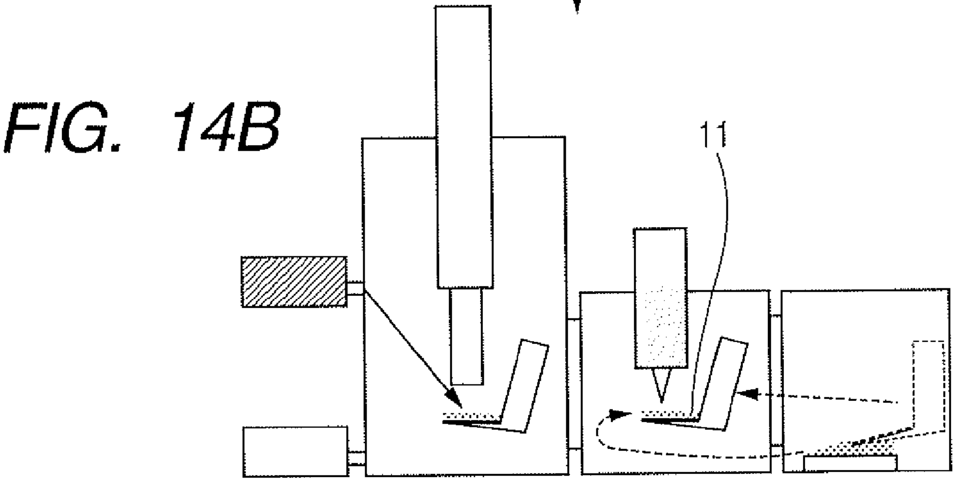

(TOF-SIMS analysis wherein a biological tissue is cut with a gold-deposited blade in a load lock chamber, and the blade having the biological tissue slice adhering thereon is transferred for the analysis to an analysis chamber, as shown in FIGS. 14A and 14B)

In this example, polypeptides of a biological tissue slice cut with a gold-deposited blade are subjected to TOF-SIMS analysis in the same manner as in Example 1 except for the following points.

As shown in FIGS. 14A and 14B, the blade having the biological tissue slice adhering thereon is transferred to the solution supplying chamber 13 and an enzyme solution is supplied thereto by ink jet operation.

Figure 14C:
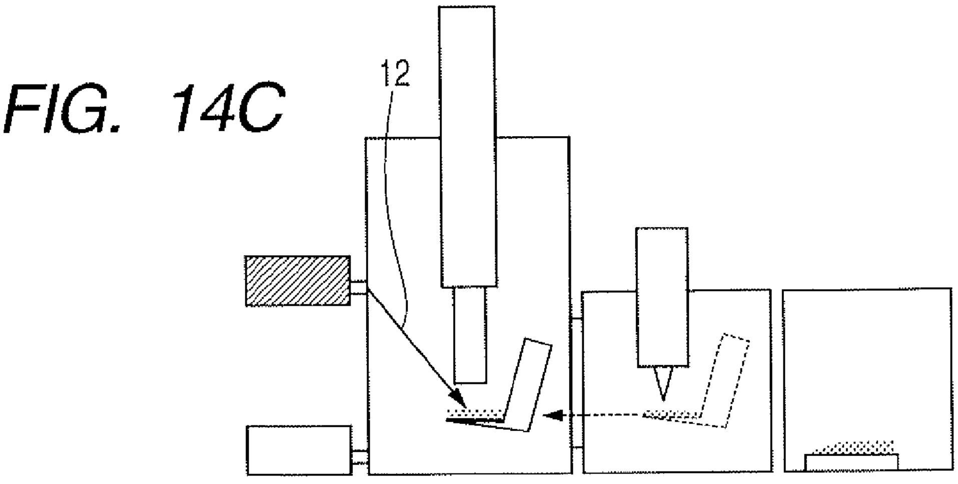

Specifically, the biological tissue slice 11 (FIG. 4A) is transferred to the solution supplying chamber 13 such that it is horizontally laid right under the ink jet 14 (FIG. 14B). Then, an enzyme solution containing trypsin in a phosphate buffer (pH 7.4) is supplied onto the slice 11 by ink jet operation under the conditions of ambient temperature and atmospheric pressure. One hour later, the ink jet is treated to prevent the solution from being discharged and the solution supplying chamber is evacuated. When the chamber is sufficiently evacuated, the biological tissue adhering onto the upper surface of the blade is dried as water contained in the tissue is sublimated while the other contents of the tissue is kept on the blade (FIG. 4B). The sample slice at this stage has a thickness of about 20 nm. Thereafter, the biological tissue sample 11 is transferred to the analysis chamber 2 such that the slice is laid horizontally right under the TOF-SIMS detector 10 (FIG. 14C).

The embodiments of the present invention as described above are capable of performing high-sensitivity time-of-flight mass spectrometry and imaging while holding the positional accuracy of a slice of a sample existing on a blade after cutting of the held sample with the blade in the apparatus.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2006-066026, filed Mar. 10, 2006, which is hereby incorporated by reference herein in its entirety.

What is claimed is:

1. A mass spectrometer comprising: a slice preparing section for preparing a slice of a sample for analysis; and a mass spectrometry section for performing time-of-flight mass spectrometry on the slice of the sample prepared in the slice preparing section, wherein the slice preparing section comprises: a sample holding mechanism for holding a sample; a blade having a metal thin film on a blade surface at least in part; and a blade position control mechanism for controlling the position of the blade and thereby performing both sample cutting and mounting of the slice of the sample obtained by cutting onto the blade surface, and wherein the mass spectrometry section comprises: a blade holding mechanism for holding the blade; and a beam irradiation mechanism for irradiating the blade surface having the slice of the sample mounted thereon with one of pulse laser and pulse ion beams.

2. The mass spectrometer according to claim 1, wherein the blade is position-controlled to keep the blade surface upward during the sample cutting.

3. The mass spectrometer according to claim 1, wherein the metal thin film is a gold thin film.

4. The mass spectrometer according to claim 1, wherein one of the pulse laser and pulse ion beams has a picosecond to nanosecond pulse width.

5. The mass spectrometer according to claim 1, wherein a region provided with the sample holding mechanism and a region receiving the beam irradiation are each capable of being independently subjected to temperature- and humidity-control.

6. The mass spectrometer according to claim 1, wherein the sample includes a polypeptide.

7. The mass spectrometer according to claim 1, wherein the mass spectrometry is time-of-flight secondary ion mass spectrometry.

8. The mass spectrometer according to claim 1, further comprising a droplet supplying mechanism for supplying droplets to the slice of the sample adhering on the blade surface.

9. A mass spectrometry method for performing time-of-flight mass spectrometry comprising irradiating a slice of a sample with one of pulse laser and pulse ion beams and thereby ionizing a molecule within the slice of the sample, wherein a sample is cut with a blade having a metal thin film on a blade surface at least in part, and the slice of the sample adhering to the blade surface is irradiated with one of pulse laser and pulse ion beams.

10. The mass spectrometry method according to claim 9, wherein a digestive enzyme solution is supplied to the slice of the sample adhering on the blade surface.

* * * * *